United States Patent [19]
Grasshoff

[11] 3,984,472
[45] Oct. 5, 1976

[54] PREPARATION OF N,N-DIALKYL P-VINYL ANILINES

[75] Inventor: J. Michael Grasshoff, Hudson, Mass.

[73] Assignee: Polaroid Corporation, Cambridge, Mass.

[22] Filed: June 27, 1974

[21] Appl. No.: 483,663

[52] U.S. Cl. .............................. 260/577; 260/574; 260/575
[51] Int. Cl.² ......................................... C07C 87/62
[58] Field of Search ................... 260/577, 575, 574

[56] References Cited
UNITED STATES PATENTS 3,709,690   1/1973   Cohan et al. ..................... 96/67

*Primary Examiner*—Robert V. Hines
*Attorney, Agent, or Firm*—Esther A. H. Hopkins

[57] ABSTRACT

A process of forming a dye mordant precursor for a photographic system by reacting a p-amino phenethyl alcohol with a trialkyl phosphate at a controlled temperature, and dehydrating the resultant p-dialkyl amino phenethyl alcohol with a strong alkali in the presence of a polymerization inhibitor.

5 Claims, No Drawings

PREPARATION OF N,N-DIALKYL P-VINYL ANILINES

This invention relates to novel chemical processes and more particularly to novel improved processes of preparing N,N,dialkyl-p-vinyl anilines.

BACKGROUND OF THE INVENTION

Polymeric compounds based on quaternized N,N,dialkyl-p-vinyl anilines are good mordants for dyes used in photographic systems. See, for example, U.S. Pat. No. 3,709,690. The usual procedure for preparing the mordant is to polymerize an N,N,dialkyl-p-vinyl aniline by radical initiation, then to quaternize the resultant homopolymer. The N,N,dialkyl-p-vinyl aniline is usually prepared by a Grignard reaction of a p-dialkyl amino benzaldehyde with methyl magnesium halide to form a p-dialkyl amino-α-methylbenzyl alcohol, which alcohol is pyrolyzed to the desired dialkyl-p-vinyl aniline. While the just-recited method uses rather inexpensive starting materials, scale-up problems arise because of the large quantities of diethyl ether required as a solvent for the Grignard reaction part of the process. In the case of the preparation of N,N-dimethyl-p-vinyl aniline, a typical member of this class of materials, the overall yield of pure monomer approaches fifty percent at best.

OBJECTS OF THE INVENTION

One object of this invention, therefore, is to provide an improved process for preparing compositions useful as starting materials for a polymeric mordant for dyes useful in photographic systems.

Another object of this invention is to provide improved processes for preparing N,N,dialkyl-p-vinyl anilines whereby increased yields may be obtained.

More specifically, it is an object of this invention to provide an improved synthesis of dialkyl-p-vinyl anilines by the dehydration of dialkyl amino phenethyl alcohols prepared by alkylation of p-amino phenethyl alcohols.

The invention accordingly comprises the several steps and the relation and order of one or more of such steps with respect to each of the others which are exemplified in the following detailed disclosure, and the scope of the application of which will be indicated in the claims.

DETAILED DESCRIPTION OF THE INVENTION

It has been found that N,N,dialkyl-p-vinyl anilines can be prepared in a straightforward one-batch process which consists of reacting a p-amino phenethyl alcohol with a trialkylphosphate followed by dehydration of the intermediate formed, a p-dialkyl amino phenethyl alcohol. The reaction of the p-amino phenethyl alcohol with the trialkylphosphate is carried out at an elevated temperature, at least as high as 130° C. but no higher than about 170° C. according to this reaction.

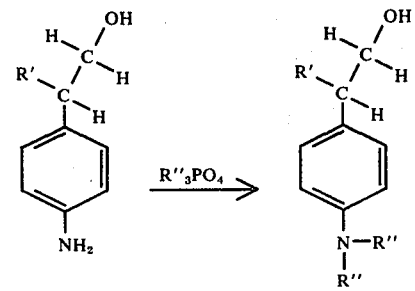

This reaction, in which R' is either a hydrogen, methyl or ethyl group and R'' is a lower alkyl group containing from one to five carbon atoms, may be carried out in the presence of a proton acceptor such as, for example, sodium bicarbonate. The use of a proton acceptor renders the reaction easier to control and prevents the formation of polyphosphate. It is important that the temperature of the reaction be maintained above about 130° C. to avoid side reactions such as O-alkylation and that the temperature be maintained below about 170° C. to avoid polymerization.

The p-dialkyl amino phenethyl alcohol thus formed is dehydrated to an N,N,dialkyl-p-vinyl aniline without the necessity of isolating the intermediate by the addition to the reaction medium of a strong alkali such as, for example, sodium hydroxide, potassium hydroxide or the like, in the presence of a material which will inhibit polymerization, such mixture being present in a catalytic amount. This dehydration reaction is effected at a temperature above 110° C. but below the boiling point of the phosphate.

Infrared analysis of the products resulting from the use of the process of the present invention show the products to have spectra identical to those of samples prepared by different techniques. The products may be used to form a dye mordant for a photographic system as disclosed in the aforementioned U.S. Pat. No. 3,709,690.

The following nonlimiting example illustrates the preparation of an N,N,dialkyl-p-vinyl aniline within the scope of the present invention.

EXAMPLE

A mixture of 137 g (1 mole) of p-amino phenethyl alcohol and 97 g (1.1 moles) of $NaHCO_3$ was heated in a 1-liter 4-necked flask, equipped with stirrer, dropping funnel, thermometer and reflux condenser. After melting of the alcohol had taken place, the flask temperature was allowed to rise to 145°. Then, 130 ml (1.1 moles) of trimethylphosphate was added at 145°–150° with vigorous stirring over a period of about 1 hour. The reflux condenser was replaced by a distilling head and the mixture was gradually heated to 180°–185° and kept at 185° for 2 hours, while taking off methanol and water. During this heating cycle a clear, homogeneous liquid was formed. The mixture was allowed to cool to 110°, followed by the addition of 0.3 g of cuprous chloride and 0.5 g of copper powder. Powdered KOH (170 g) was added in small portions so as to keep the temperature between 110° and 130°. A water aspirator vacuum was applied at 120° for about 1 hour to remove volatiles. The stirrer was removed and an oil pump vacuum (0.2–0.5 mm) was applied. The flask contents were heated to 190° and maintained there for a total of 10 hours. A pale yellow pyrolysate (105 g) was collected (vapor temperature range 60°–120°). Fractionation at 0.3 mm gave 78 g (53%) of a colorless liquid, $b_{0.3}$ 65°, that solidified in the refrigerator (m.p. 17°).

Anal. Calculated for $C_{10}H_{13}N$: C, 81.6; H, 8.9; N, 9.5. Found: C, 81.9; H, 8.9; N, 9.3.

Since certain changes may be made in the above process without departing from the scope of the invention herein involved, it is intended that all matter contained in the above description shall be interpreted as illustrative and not in a limiting sense.

What is claimed is:

1. The process of forming a dialkyl-p-vinyl aniline which comprises:
    a. reacting a p-amino phenethyl alcohol of the formula:

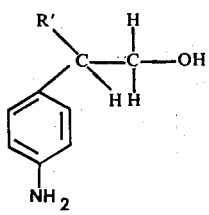

wherein R' is selected from the group consisting of hydrogen, methyl and ethyl groups, with a trialkyl- phosphate $R''_3PO_4$ wherein R'' is selected from the group consisting of alkyl radicals of from one to five carbon atoms at a temperature of at least 130°C. but no higher than 170°C. to form a p-dialkyl amino phenethyl alcohol, and
    b. dehydrating said p-dialkyl amino phenethyl alcohol at a temperature of at least 110° by the addition of a strong alkali in the presence of a polymerization inhibitor to form a dialkyl-p-vinyl aniline.

2. The process of claim 1 wherein said p-amino phenethyl alcohol reacts with said trialkylphosphate in the presence of a proton acceptor.

3. The process of claim 1 wherein said trialkyl phosphate is trimethylphosphate.

4. The process of claim 1 wherein said polymerization inhibitor comprises a mixture of cuprous chloride and copper powder.

5. The process consisting essentially of:
    a. reacting 2,-(p-amino phenyl) ethanol with trimethyl phosphate at a temperature of at least 130° but no higher than 170° in the presence of a proton acceptor to form 2,-(N,N,dimethyl amino phenyl) ethanol, and
    b. dehydrating said 2,-(N,N,dimethyl amino phenyl) ethanol at a temperature of at least 110° in the presence of catalytic amounts of cuprous chloride and copper powder to form N,N,dimethyl-p-vinyl aniline.

* * * * *